US009456768B2

(12) United States Patent
Soatto et al.

(10) Patent No.: US 9,456,768 B2
(45) Date of Patent: Oct. 4, 2016

(54) SPIROMETRY SYSTEM AND DISPOSABLE VOLUME SPIROMETRY APPARATUS

(76) Inventors: Stefano Soatto, Pasadena, CA (US); Giuseppe Torresin, Padua (IT)

(*) Notice: Subject to any disclaimer, the term of this patent is extended or adjusted under 35 U.S.C. 154(b) by 431 days.

(21) Appl. No.: 13/212,984

(22) Filed: Aug. 18, 2011

(65) Prior Publication Data

US 2012/0046568 A1 Feb. 23, 2012

Related U.S. Application Data (60) Provisional application No. 61/374,818, filed on Aug. 18, 2010.

(51) Int. Cl.
*A61B 5/08* (2006.01)
*A61B 5/087* (2006.01)
*A61B 5/093* (2006.01)

(52) U.S. Cl.
CPC ............. *A61B 5/0873* (2013.01); *A61B 5/093* (2013.01)

(58) Field of Classification Search
USPC .......................................................... 600/540
See application file for complete search history.

(56) References Cited

U.S. PATENT DOCUMENTS

| 4,291,704 A * | 9/1981 | Petty et al. .................... 600/541 |
| 4,996,642 A | 2/1991 | Hey |
| 5,576,778 A | 11/1996 | Fujie et al. |
| 5,983,201 A | 11/1999 | Fay |
| 6,231,188 B1 | 5/2001 | Gao et al. |
| 2002/0101594 A1* | 8/2002 | Slatter ........................... 356/601 |
| 2003/0028120 A1* | 2/2003 | Mault et al. ................... 600/531 |
| 2005/0075552 A1* | 4/2005 | Schmidt et al. ............... 600/364 |

OTHER PUBLICATIONS

Soatto, Luigi Ricciato-Stefano. "ICPSAC: A New Robust and Accurate Registration Algorithm." (2007).*
Soatto, Stefano "3-D Structure from Visual Motion: Modeling, Representation and Observability" Automatic, vol. 33, No. 7, pp. 1287-1312, 1997 Elsevier ScienceLtd.*
Ma, Yi, et al. "Step-by-Step Building of a 3-D Model from Images." An Invitation to 3-D Vision. Springer New York, 2004. 375-411 together with software distributed at http://vision.ucla.edu/MASKS.*
McInerney, T., "Topology Adaptive Deformable Surfaces for Medical Image Volume Segmentation" IEEE Transactions on Medical Imaging, vol. 18, No. 10, Oct. 1999 (McInerney).*
Jackson, Jeremy D., Anthony J. Yezzi, and Stefano Soatto. "Dynamic shape and appearance modeling via moving and deforming layers." International Journal of Computer Vision 79.1 (2008): 71-84.*

(Continued)

*Primary Examiner* — Michael Kahelin
*Assistant Examiner* — Mitchell E Alter
(74) *Attorney, Agent, or Firm* — Steinfl & Bruno, LLP (57) ABSTRACT

A disposable volume spirometry apparatus and non-contact measurement system is described. The spirometry system includes an expandable disposable volume spirometry apparatus, a remote non-contact sensor, memory, and a processor. The remote non-contact sensor captures images associated with the expandable disposable volume spirometry apparatus. The memory stores the captured images. The processor is operatively coupled to the memory and determines a volume for the expandable disposable volume spirometry apparatus by analyzing the captured images.

20 Claims, 5 Drawing Sheets

(56) References Cited

OTHER PUBLICATIONS

Blake, Andrew et al., "Active Contours", Springer-Verlag, 1998, pp. 97-113.

Bachnak, Rafic et al., "A Stereo System for 3-D Measurement in Robot Workspaces", IEEE International Symposium on Intelligent Control, 1989, pp. 293-298.

Burl, M.C. et al., "Face Localization via Shape Statistics", International workshop on face and gesture recognition, Zurich, Switzerland, Jun. 1995.

Tsai, Roger, "An Efficient and Accurate Camera Calibration Technique for 3D Machine Vision", IEEE Transactions on Robotics and Automations, 1996, pp. 364-374.

Mirtich, B. "Fast and Accurate Computation of Polyhedral Mass Properties" J. of Graphics Tools, vol. 1, No. 2, 1996. 15 pages.

* cited by examiner

SPIROMETRY SYSTEM AND DISPOSABLE VOLUME SPIROMETRY APPARATUS

CROSS-REFERENCE

This patent application claims the benefit of provisional patent application 61/374,818 filed on Aug. 18, 2010 and entitled DISPOSABLE VOLUME SPIROMETRY APPARATUS.

FIELD

The present invention relates to a disposable volume spirometry apparatus and non-contact measurement system. More particularly, the present invention relates to a spirometry system that determines the volume of the disposable volume spirometry apparatus using image analysis and a remote sensor.

BACKGROUND

Measurements of airflow and volume are regularly performed during clinical investigations in respiratory physiology and pathology, occupational medicine, sports medicine, allergy and immunology, respiratory function laboratories, pulmonology, as well as in a variety of industrial and scientific settings. Spirometry is a non-invasive method of lung function testing that measures the amount (volume) and/or speed (flow) of air that can be inhaled and exhaled. Spirometry generates measurements that are helpful in assessing conditions such as asthma, chronic bronchitis, emphysema, chronic obstructive pulmonary disease (COPD), pulmonary fibrosis, cystic fibrosis, and other such lung related conditions.

For example, the incidence of chronic obstructive pulmonary disease (COPD) has escalated in recent years and is now the fourth leading cause of death in the US, at 121,000 fatalities per year. Prevalence of severe COPD among individuals aged 40 and older is estimated to be at 10%. The prevalence of asthma is even higher. The cost to the health care system of dealing with COPD was estimated at over 32 Billion US Dollars in 2002. (European Union Conference on Chronic Respiratory Disease: Purpose and Conclusions, M. Decramer et al.) Effectively managing COPD requires early detection and prediction, affecting the natural course of the disease, and improving management with optimized intervention.

Spirometry measurements are usually performed in two distinct ways: via a volume measurement device, or via a flow measurement device. In operation, spirometry measures the volume and/or flow of air that is exhaled or inhaled. The spirometry test is performed using a device called a spirometer that displays graphs called spirograms. Spirograms include a volume-time curve showing the volume, e.g. liters, on the y-axis and time, e.g. seconds, along the x-axis. The spirograms also include a flow-volume loop that graphically depicts the rate of airflow on the y-axis and the total volume inhaled and exhaled on the x-axis.

Previously, volume measurements were performed in a number of ways, using a "bell" spirometer or a "bag-in-box" device where an inflatable element, i.e. "bag", is enclosed in an air-tight element, i.e. "box" that is physically connected to external air through a flow meter. The purpose of the box was not only to contain the bag, but also to serve as a primary measurement device, where the volume contained by the bag is determined as a function of the pressure or residual volume in the box. The bag-in-box is no longer used because the device is bulky, leaks, and requires airproofing after the internal bag is changed.

Figure 1A:
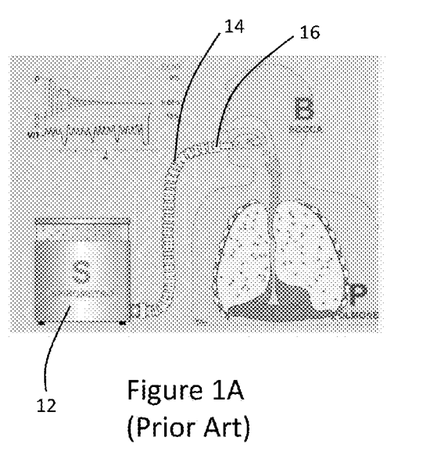
FIG. 1A shows a prior art volume spirometer, in which a patient is starting to exhale into mouthpiece, the flexible tube, the inner tubing of the spirometer and the movable bell.

Referring to FIG. 1A there is shown a prior art "bell" volume spirometer, in which a patient is starting to exhale into mouthpiece, the flexible tube, the inner tubing of the spirometer and the movable bell. The volume spirometer includes a moving chamber 12 or "bell", a breathing tube 14, and a mouthpiece 16.

Figure 1B:
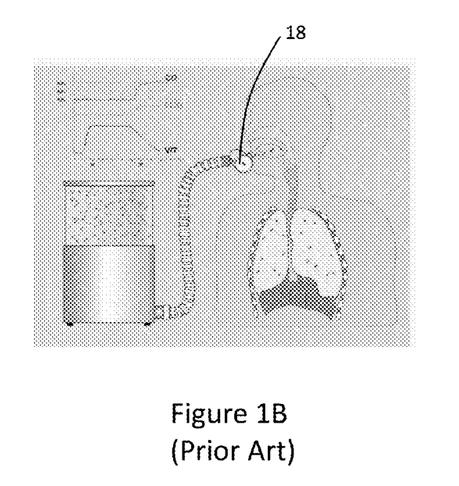
FIG. 1B shows the prior art volume spirometer of FIG. 1A after the patient has completed exhaling and a single-breath measurement with no circulation through a soda lime receptacle for the prior spirometer in FIG. 1A.

Referring to FIG. 1B there is shown the prior art volume spirometer of FIG. 1A after the patient has completed exhaling and a single-breath measurement with no circulation through a soda lime receptacle. In FIG. 1B the volume spirometer includes a valve 18 and the similar components of the volume spirometer of FIG. 1A.

Figure 1C:
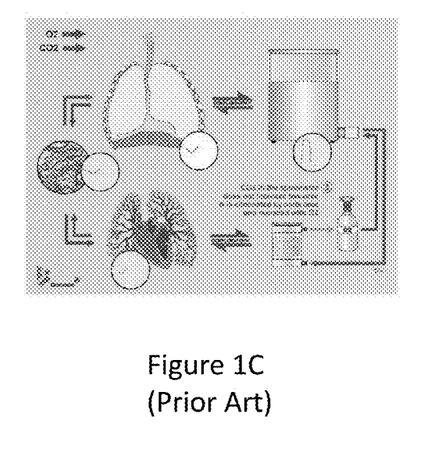
FIG. 1C shows a prior art system for rebreathing with $CO_2$ removal through soda lime.

In FIG. 1C, there is shown the air flow during rebreathing and the chemical process for $CO_2$ removal. In the rebreathing system, the $CO_2$ exhaled by the patient does not increase in the bell because the $CO_2$ is removed by the soda lime and replaced with $O_2$.

Figure 1D:
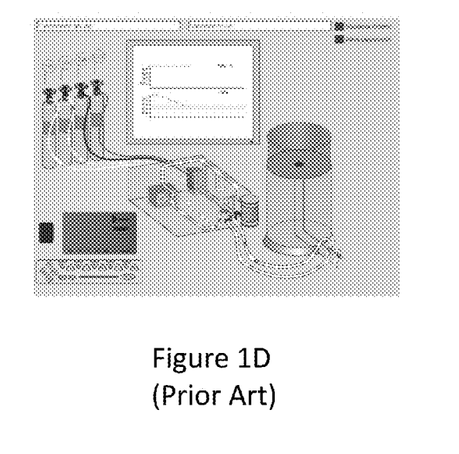
FIG. 1D shows a prior art rebreathing system that uses the movable bell of FIG. 1A.

Referring now to FIG. 1D, there is shown a prior art rebreathing system that uses the movable bell of FIG. 1A. The rebreathing system includes the movable bell, an inlet valve represented as a red valve, an outlet valve represented as a blue valve, a soda lime receptacle, an electric pump, and a variety of different tubes.

The volume-measurement spirometer measures the volume of a particular gas entering the moving bell that rises and falls under the competing action of gravity and pressure from the gas pushed inside the chamber during the measurement session. The change in volume is typically measured electromechanically by encoders electrically coupled to transducers and suitable electronic circuitry or digital hardware and software that convert the measurements of displacement of the bell into measurements of volume within the chamber. Although this instrumentation is mature, reliable, and precise, the spirometric instrumentation is cumbersome and not very portable. Additionally, even if the bell spirometer is movable, it must be calibrated and retested after being moved.

There are also additional components and actions that must be taken to sanitize the volume-measurement spirometer. Since different patients breathe in and out of the same instrument, this results in the potential spread of disease and precautionary measures must be taken including using filters and membranes, and periodically sterilizing the spirometer. These sanitary measures also add to the expense of the operation and maintenance of the traditional spirometer.

The flow-measurement spirometer measures flow, not volume, and obtains a volume measurement by post-processing flow data. The flow-measurement spirometer includes peak-flow meters and pneumotachographs. The flow-measurement spirometer devices are smaller and more portable. However, the flow-measurement spirometer is also more sensitive to drift and accumulation errors, and is considered less accurate, precise and reliable than the volume-measurement spirometer.

In operation, the volume-measurement and flow-measurement devices are typically placed in contact with the patient by providing a disposable mouthpiece that is usually made of cardboard, but often also plastic. The patient proceeds to hold either a flexible tube or mask for volume device, or the flow device itself and then perform the test procedure that may involve re-breathing. The disposable mouthpiece is then replaced after patient use.

When the spirometer is used, the patient exhales an air mixture with droplets of saliva and pathogens that come into contact with various working components of the spirometer that are not disposed of. For example, the flexible tube and moving chamber that comes in contact with the patient's exhaled breath is not disposed of after patient usage.

The next patient that uses the spirometer may inhale pathogens or droplets of saliva from either the chamber or through the flow sensor. This phenomenon is minimized, but not eliminated, by the use of filters as well as periodic cleaning and sterilization of the entire instrument ensemble. Additionally, the cost of periodically sterilizing the spirometer is significant, so the sterilization operation cannot be performed after every patient. Furthermore, even if cleaning was performed after each patient, there is no guarantee that spirometer instrumentation would be sterile. Further still, the measurement devices must also be cleaned and disinfected periodically in order to avoid growth of molds and pathogens; and this cleaning procedure requires the measurement device to be disassembled and re-calibrated.

In summary, a sterile environment cannot be ensured by simply replacing the cardboard mouthpiece of either the volume measurement device or flow measurement device.

SUMMARY

A disposable volume spirometry apparatus and non-contact measurement system is described. In a first embodiment, the spirometry system includes an expandable disposable volume spirometry apparatus, a remote non-contact sensor, memory, and a processor. The remote non-contact sensor captures optical images and/or range images associated with the expandable disposable volume spirometry apparatus. The memory stores the captured images. The processor is operatively coupled to the memory and determines a volume for the expandable disposable volume spirometry apparatus by analyzing the captured images.

In another embodiment, the spirometry system includes an expandable disposable volume spirometry apparatus that further includes a first valve that allows air to enter the expandable disposable volume spirometry apparatus, a filter element that captures carbon dioxide, and a second valve that allows air to exit the expandable disposable volume spirometry apparatus. The remote non-contact sensor is configured to capture a plurality of images associated with the expandable disposable volume spirometry apparatus. The processor is operatively coupled to the memory, and the processor is configured and/or programmed to determine a volume for the expandable disposable volume spirometry apparatus by analyzing the captured images. In operation, the carbon dioxide ($CO_2$) associated with an exhaled gas mixture passes the first valve, enters the expandable disposable volume spirometry apparatus, and is captured by the filter element before the second valve allows the exhaled gas mixture to exit the expandable disposable volume spirometry apparatus.

In yet another embodiment, the spirometry system includes a projector that generates a light pattern that is projected on the expandable disposable volume spirometry apparatus. The remote non-contact sensor then captures the images of the light pattern projected on the expandable disposable volume spirometry apparatus. The memory stores the captured images. The processor determines a volume for the expandable disposable volume spirometry apparatus by extrapolating a three-dimensional estimate of the expandable disposable volume spirometry apparatus.

In yet another embodiment, the spirometry system includes a range measurement device, including a time-of-flight camera, a laser or lidar, a structured-light sensor, or other device that provides a range map (a.k.a. range image) from which a volume measurement can be inferred.

In yet another embodiment, the spirometry system includes an inflatable element that is patterned with a known pattern with high photometric saliency, so that the deformation of the pattern induced by inflation, once measured through one or more imaging devices, can be related to range, and thence volume, through methods described in Y. Ma, S. Soatto, J. Kosecka, S. Sastry, "An Invitation to 3-D Vision", Springer Verlag, 2003, or P. Favaro and S. Soatto, "3-D Shape Estimation and Image Restoration", Springer Verlag, 2006.

DRAWINGS

The present invention will be more fully understood by reference to the following drawings which are for illustrative, not limiting, purposes.

DETAILED DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the devices, systems, and methods described hereinafter may vary as to configuration and as to details.

The disposable volume spirometry apparatus and non-contact measurement described herein replaces the movable bell spirometer, breathing tube, mouthpiece and the rebreathing system described above. The spirometry system and expandable disposable volume spirometry apparatus described here perform volume measurements using remote sensing measurements, as opposed to pressure measurements or indirect flow measurements, thereby overcoming the limitations of the previously disclosed devices. The remote sensing methods described herein rely on computer vision technology to infer volume from imaging data, that could be in the visible or other spectra (infra-red, laser, LIDAR, structured light, time-of-flight, etc.).

Figure 2:
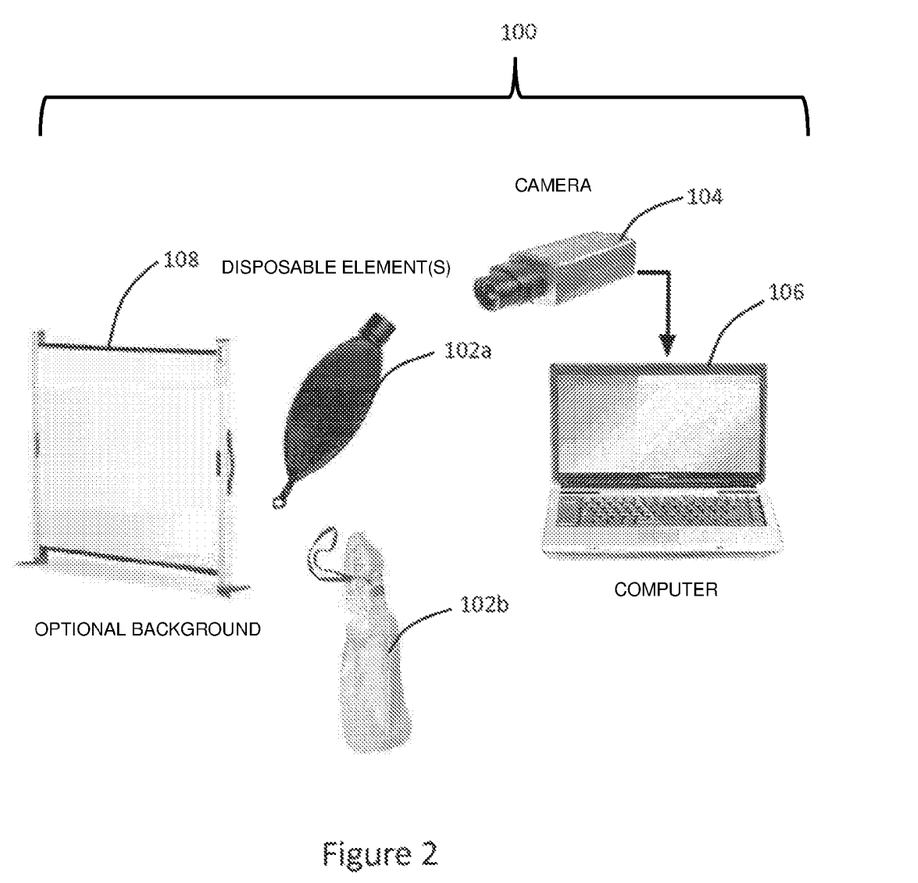
FIG. 2 shows an illustrative disposable volume spirometry apparatus and non-contact measurement system.

Referring to FIG. 2 there is shown an illustrative embodiment of a disposable volume spirometry apparatus and non-contact measurement system. The illustrative spirometry system 100 includes an expandable disposable volume spirometry apparatus 102, a remote non-contact sensor 104, and a computer 106 that includes a memory and a processor. The remote non-contact sensor 104 captures images associated with the illustrative expandable disposable volume spirometry apparatus 102a or 102b. The memory stores the captured images. The processor is operatively coupled to the memory and determines a volume for the expandable disposable volume spirometry apparatus by analyzing the captured images as described herein.

The disposable volume spirometry apparatus 102 may be composed of different materials, have different shapes and different colors. In the general, the disposable volume spirometry apparatus 102 is composed of an expandable elastomeric material, and possibly a "skeleton" made of different materials. Thus, the disposable volume spirometry apparatus 102 operates like an inflatable balloon-like device. Additionally, the disposable spirometry apparatus may be composed of an opaque material 102a or a translucent material 102b. The disposable spirometry apparatus 102 may also include a pattern (not shown) disposed thereon to remove dependency on calibration and improve the robustness of the vision algorithms. In operation, a patient can exhale and inhale into the disposable volume spirometry apparatus 102.

The spirometry system 100 may also include a background 108 that is detached from the disposable spirometry apparatus 102. The background 108 can also be configured to encase the disposable spirometry apparatus 102 such as in the bag-in-box implementation described previously.

In one illustrative embodiment, the remote non-contact sensor 104 is a digital camera that captures an occluding boundary projected on the background. The occluding boundary or silhouette corresponds to the expandable disposable volume spirometry apparatus 102a or 102b. Alternatively, the remote non-contact sensor 104 may include a range sensor, a laser-based remote sensor, a radar-based remote sensor, a plurality of remote sensors, or any combination thereof. This remote non-contact sensor 104 includes so-called time-of-flight cameras or structured light sensors as employed in the recent KINECT® distributed by Microsoft Corp, in which the spirometry system 100 operates using a structured light that projects an infrared light with a known pattern onto the disposable volume spirometry apparatus 102 and the computer 106 proceeds to read the deformation of the pattern optically using a standard or special-purpose camera 104, e.g. a camera with infra-red filters.

Figure 3A:
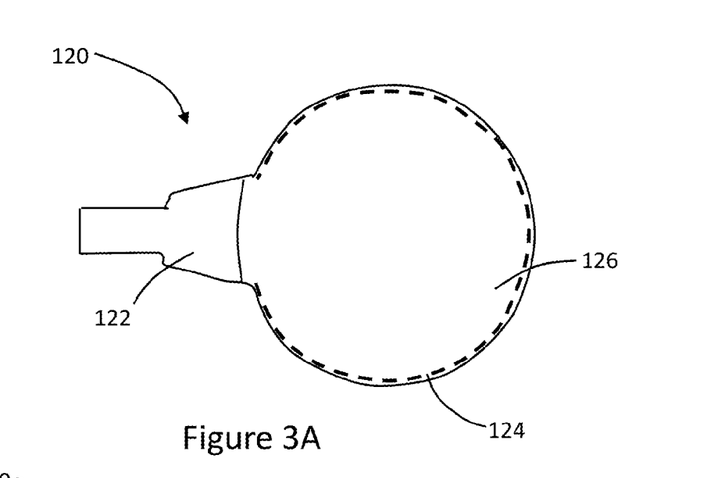
FIG. 3A-3C show a disposable volume spirometry apparatus without a rebreather component.
Figure 3B:
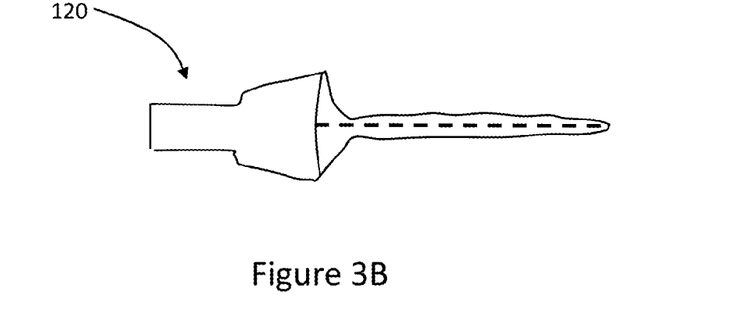
Figure 3C:
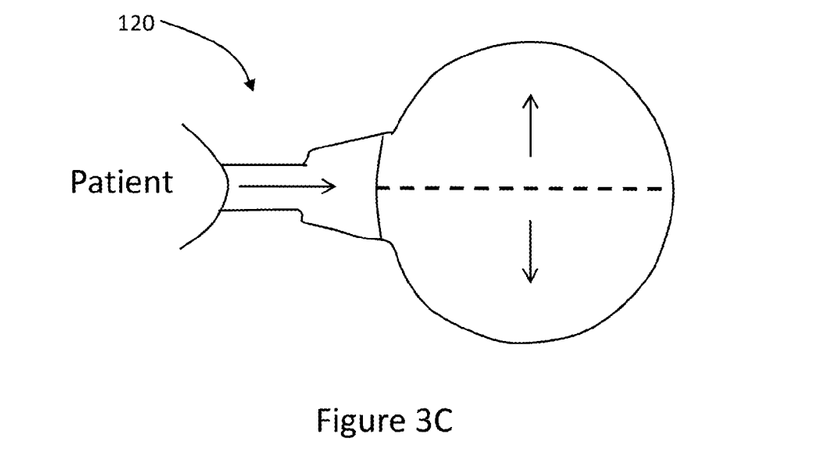

Referring to FIGS. 3A-3C there is shown an illustrative disposable volume spirometry apparatus without a rebreather, which is also referred to as a single-breath or single-volume embodiment. In FIG. 3A, a top view of the illustrative disposable volume spirometry apparatus 120 is shown. A mouthpiece 122 is configured to fit the patient's mouth. In the illustrative embodiment, the mouthpiece 122 interfaces with a structural component 124 that provides a structural perimeter for interfacing with an elastomeric membrane 126.

By way of example and not of limitation, the elastomeric membrane 126 includes two deformable membranes fixed to an oval sheet of porous membrane with the structural component 124. For example, the structural component 124 may be a non-deformable plastic border, with an equivalent diameter of 30 cm and an approximate area of 700 $cm^2$, a thickness of 3 mm, and a weight of approximately 150 grams. The two deformable membranes may be adhesively coupled to the structural component 124 by using an annealing process or an adhesive or any combination thereof. The shape of the membrane appears similar to a leaf, an oval shape with an elongated portion that extends toward the mouthpiece 122. By way of example and not of limitation, the mouthpiece is approximately 3 centimeters in diameter and 4 centimeters long.

In FIG. 3B, there is shown a side view of the illustrative volume spirometry apparatus 120. Since the patient has not exhaled into the disposable volume spirometry apparatus 120, there is little or no empty space in the elastomeric membrane 126. For some applications, the inflatable element can have zero volume at rest. This means that the inflatable element can be flat, or can take the configuration and volume determined by the skeleton of the inflatable element and the elastic properties of the inflatable material. In FIG. 3C, there is shown a side view of the volume spirometry apparatus after the patient has exhaled and the elastomeric member an 126 has expanded accordingly.

Depending on the sensor type and analytical method used to measure volume, the elastic properties of the disposable volume spirometry apparatus may be used to extrapolate independent volume measurements on a controlled sample (training set) to the test at hand (test set). This approach requires the disposable element to be manufactured to sufficient precision as to yield repeatable measurements to within the accuracy prescribed by the American Thoracic Society (ATS). Additionally, the disposable volume spirometry apparatus may have different sizes to obtain the maximum accuracy for volume measurements (for instance, adult male, adult female, child, senior person etc.). Some embodiments do not require accurately predictable or repeatable material specifications and manufacturing process, as volume is measured directly rather than extrapolated by using material properties.

Figure 4A:
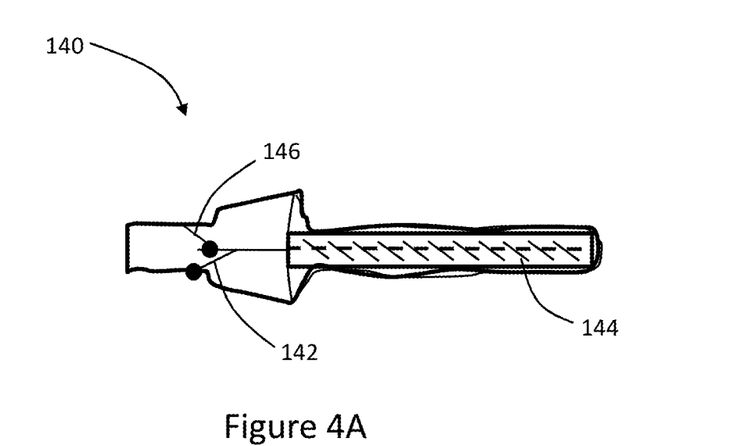
FIG. 4A and 4B show a disposable volume spirometry apparatus that includes a rebreather component.
Figure 4B:
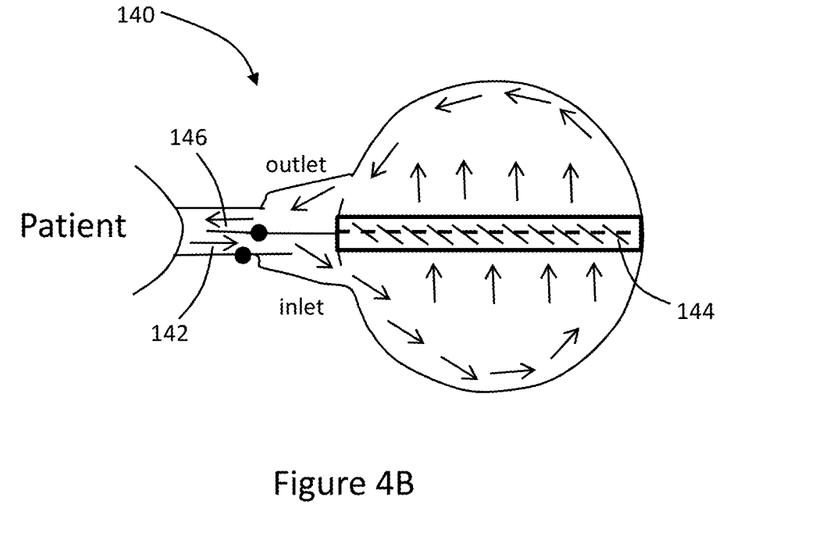

Referring to FIGS. 4A-4B there is shown a disposable volume spirometry apparatus that includes a rebreather component. The rebreathing disposable volume spirometry apparatus 140 includes the mouthpiece, the structural component and the elastomeric membranes as described above in FIGS. 3A-3C.

In FIG. 4A there is shown the rebreathing disposable volume spirometry apparatus 140 in a deflated mode, in which the patient has not exhaled into the disposable volume spirometry apparatus 140. The rebreathing apparatus 140 includes a first valve 142 that allows a gas mixture to enter the expandable disposable volume spirometry apparatus, a filter element 144 that captures carbon dioxide, and a second valve 146 that allows the gas mixture to exit the expandable disposable volume spirometry apparatus. In the deflated mode, there is as little dead volume as possible. Dead volume is the volume of air between the patient's airways and the functional elements of the spirometer.

As described in this patent, a remote non-contact sensor is configured to capture a plurality of images associated with the expandable disposable volume spirometry apparatus. The processor is operatively coupled to the memory, and the processor is configured to determine a volume for the expandable disposable volume spirometry apparatus by analyzing the captured images.

Referring to FIG. 4B there is shown the rebreathing disposable volume spirometry apparatus in an inflated mode, in which the patient has exhaled into the disposable volume spirometry apparatus. In operation, the carbon dioxide ($CO_2$) associated with an exhaled gas mixture passes the first valve 142, enters the expandable disposable volume spirometry apparatus, and is captured by the filter element 144 before the second valve 146 allows the exhaled gas mixture to exit the expandable disposable volume spirometry apparatus.

By way of example and not of limitation, the filter element 144 is composed of a porous membrane that uses soda lime to trap carbon dioxide ($CO_2$). Additionally and/or alternatively, the filtering element 144 may also trap or collect specific breath trace elements such as carbon monoxide (CO), nitrogen oxide (NO), exhaled breath condensate (EBC), volatile organic compounds (VOC), and other biological fragments.

The illustrative soda lime membrane that operates as filter element 144 can be manufactured in a cost-effective manner by taking a structural mesh, made of plastic or metal, on which soda lime powder is deposited through a chemical or mechanical deposition process. In this illustrative embodiment, the soda lime membrane provides structural support for the disposable volume spirometry apparatus much like the structural component 124 described above.

The exhaled gas mixture that passes through the filter element 144 may then be sampled. The illustrative filter element 144 may be asymmetric to enable all the inhaled mixture to be filtered through the porous membrane. Additionally, the elastomeric membrane on the two sides of the disposable volume spirometry apparatus can have different resistance so as to ensure that one side is always depleted and guarantee that all exhaled air is filtered before being re-breathed so that the inflatable element on the expiratory side a bit "harder" than the one at the inspiratory side.

In one embodiment, the rebreathing disposable volume spirometry apparatus 140 is configured to be repeatably deformable and the repeatable deformable capability can be guaranteed with proper manufacturing and testing procedures. An illustrative cost effective volume element includes an inflatable double lattice leafs on a oval plastic skeleton with a cylindrical elongation toward the patient's mouth as described previously in FIGS. 3A-3C. Note that other embodiments do not require repeatability in the manufacturing process.

In another embodiment, a repeatable deformable spirometry apparatus 140 is not crucial because range measurements are performed using a range sensor that uses optical time-of-flight, structured light, LIDAR, or other such range sensor. Since the range sensor directly determines the geometry of the visible portion of the surface of the inflatable element, significant intra-individual variability among manufactured elements can be tolerated, which in turn reduces manufacturing costs.

In FIG. 3A-3C a single-volume disposable volume spirometry apparatus is described. The single-volume embodiment is applied to procedures that measure slow and forced vital capacity, respiratory pattern, maximum voluntary ventilation, chemoreceptor response to hypercapnia, and single breath administration of a gaseous mixture.

In FIG. 4A-4B a rebreathing disposable volume spirometry apparatus is presented. The rebreathing embodiment is well suited for specialized respiratory investigations, e.g. the ones for evaluating the breathing efficiency on the renewal dynamics of alveolar air (through an inert and light gas like helium), or for the response to hypoxyemia, or the stress response of carbon monoxide diffusion.

Although different manufacturing options are available for each embodiment, the exhaled gas mixture can be captured in the disposable volume spirometry apparatus in different locations such as at a patient's home, in the operating room or in the field. Additionally, the exhaled gas mixture can be stored and analyzed by other gas analyzers without the need for pumps and batteries.

Figure 5:
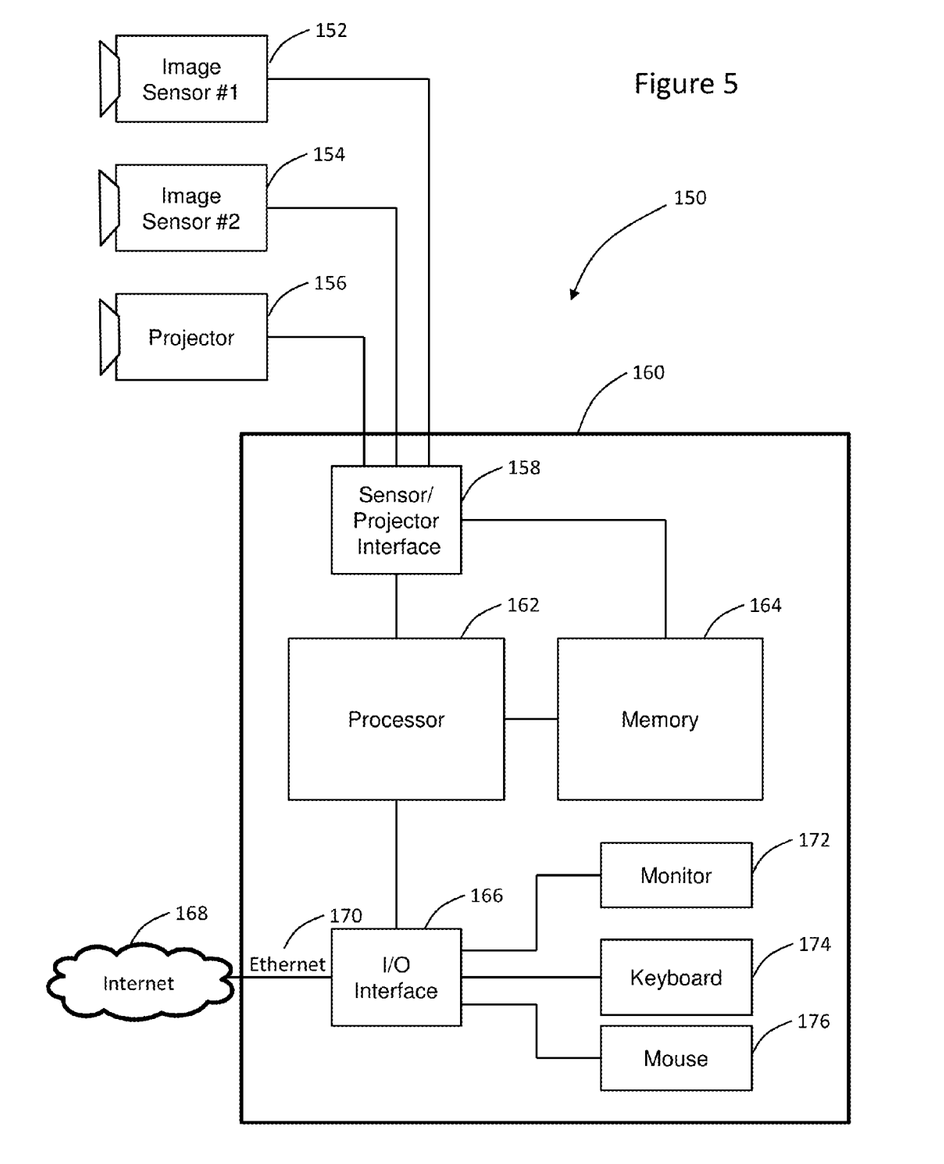
FIG. 5 shows an illustrative non-contact measurement system configured to determine the volume of the disposable volume spirometry apparatus.

Referring to FIG. 5 there is shown an illustrative non-contact measurement system 150 configured to determine the volume of the disposable volume spirometry apparatus disposable as described above.

The non-contact measurement system 150 may include one sensor 152 or a plurality of sensors such as illustrative sensors 152 and 154. The sensors 152 and 154 may be a digital camera, an electro-optical sensor, an infra-red remote non-contact sensor, including a laser-based and a radar-based sensor, and any other such optical sensor used in computer vision analysis. Additionally, a sensor may be associated with a complementary projector 156 that generates a measureable signal that is captured by illustrative sensor 154. The sensors 152 and 154 and projector 156 are communicatively coupled to interface 158, which is associated with computing device 160.

The computing device 160 includes a processor 162, memory 164 and an input/output (I/O) interface 166 that is communicatively coupled to a wide area network such as the Internet 168 via an Ethernet 170 connection. The computing device also includes a monitor 172, a keyboard 174 and mouse 176 communicatively coupled to the I/O interface 166.

The illustrative computing device 160 is operatively coupled to at least one sensor 152. The computing device 160 captures, stores and processes each measurement frame at intervals of 60 frames-per-second (FPS). The actual interval for capturing a measurement frame is dependent on engineering requirements and system limitations as well as guidelines for the specific clinical application. The illustrative computing device 160 includes storage and processing units that enable buffering and processing images and I/O ports that support communicatively coupling digital cameras using USB, Firewire or other standard connection interfaces.

The memory 164 includes two different types of memory, namely, volatile and nonvolatile memory. In the illustrative embodiment, the captured images are processed using volatile memory and stored in non-volatile memory.

The non-contact measurement system 150 may also be communicatively coupled to a server (not shown) via a wide area network such as the Internet 168 so that spirometry results may be communicated to the appropriate medical health care professional.

Furthermore, the non-contact measurement system 150 is configured to support the transfer multiple streams of images or other data types, including from multiple cameras, possibly in a synchronized manner, onto the memory 164 of the computing device 160. In the presence of multiple calibrated imaging devices, or single composite or active imaging devices including but not restricted to time-of-flight cameras, laser range finders, structured-light sensors, scale can be determined unambiguously, and therefore it is not necessary to restrict the position of the sensing element relative to the inflatable element, other than to maintain it in the field of view and within a prescribed range for measurement sensitivity.

The remote non-contact sensing device measurement systems can be used to perform remote, non-contact measurements of the volume element, including laser- and radar-based system (active measurements device), and imaging systems, including electro-optical (EO), infrared (IR), active-illumination, time-of-flight and multi-spectral imagers. By way of example and not of limitation, a standard optical camera is the simplest embodiment. However, unlike active measurement devices, the use of a passive measurement yields data (images) that depend on a number of nuisance factors such as illumination, background clutter, and distance from the object result in more processing. An active ranging measurement device, such as a structured illumination sensor, a stereo rig, or a time-of-flight camera bypass these limitations and provide a measurement of scale in a natural manner without the need to limit the mobility of the patient during the procedure (so long as she stays within the field of view of the sensor).

Depending on the embodiment, one or more cameras may be used. For instance, two or more cameras can be used to estimate the position of feature points via triangulation, as described below, following standard practice as described by Y. Ma, S. Soatto, J. Kosecka and S. Sastry, AN INVITATION TO 3D VISION, FROM IMAGES TO GEOMETRIC MODELS, Springer Verlag, 2003, which is hereby incorporated by reference.

In one illustrative embodiment, the sensor 152 captures images of the disposable volume spirometry apparatus, from which the occluding contour or "silhouette" of the projection of the inflatable elements on to the image-plane can be computed, as an intermediate step for measuring the volume of the element. Image processing is performed by the computing device 160 and the results are stored in memory 164.

For the various embodiments described above, software algorithms for geometric extrapolation of surface measurements into volume inferences can be implemented to arrive at a volume measurement.

The software algorithms receive as input one or more digitized images of the inflatable element, and produce as output an estimate of the volume of the three-dimensional region enclosed by the inflatable element. Several algorithms can be implemented, depending on the design of the inflatable element, the accuracy/computation-time tradeoff, the corresponding cost and manufacturing repeatability of the inflatable element, whether for single-breath tests or re-breathing applications, and depending on whether range measurements are available (from structure light or other ranging mechanism) or optical data alone.

In a first illustrative embodiment, the algorithms process images of the disposable element to compute the occluding boundary or the element, or to automatically select salient features within, and track them over time. In another embodiment, the algorithms process the estimated location of the silhouette, or the position and location of feature points, to estimate the three-dimensional volume of the disposable element. Also, the algorithms may be configured to locate the position in 3D of an element of the disposable component, such as the mouthpiece, to determine the absolute position, i.e. depth, to determine the overall scale of the deforming device, even in the monocular scale. See Ma, Soatto, Kosecka and Sastry, AN INVITATION TO 3D VISION FROM IMAGES TO GEOMETRIC MODELS, 2003, Springer Verlag. In Ma et al., a number of techniques are described to infer 3-D geometry from multiple views of a scene. Such multiple views could correspond to multiple images of the same scene, for instance via a stereo rig, or for structured light where the projection rays from the scene onto the sensing element of a camera is replaced by an illumination ray from an emitter to a point on the scene. The algorithms may also be configured to exploit models of the disposable device using variable geometry, or elastic properties of the materials used, in order to infer 3D volume from 2D images with one or more cameras.

Another illustrative algorithm captures an image of the solid-color inflatable element, either used in-bag or freely, in such a way that the imaging sensor captures the element against a uniform background. Computer vision algorithms can then be employed to detect the inflatable element, estimate the shape of the silhouette at each instant in time and at every frame. For example, Jackson et al. describes a method to automatically detect, track and estimate the deformation of a deforming element in imaging data, including a deforming balloon. See Jackson, Yezzi and Soatto, DYNAMIC SHAPE AND APPEARANCE MODELING VIA MOVING AND DEFORMING LAYERS, International Journal of Computer Vision, 2008, pp. 71-84, August, Vol. 79(1).

Other algorithms use the shape of the occluding boundary to infer the three-dimensional volume enclosed exploiting symmetry of the inflatable element. Note, for these algorithms it is not possible to directly determine the relation between the occluding boundary that is estimated explicitly and the symmetry plane. Therefore, the dependency has to be tabulated and depends on the physical characteristics of the inflatable element that has to be manufactured so as to be repeatable within the error bounds prescribed by ATS guidelines. Such a passive measurement modality is the simplest and most affordable because it only requires a single camera and little or no dedicated hardware such as structured illuminators or range imaging devices. However, it is more challenging to infer volume in the absence of additional measurement and illumination devices such as a structured illuminator. Nevertheless, several methods can be used to design algorithms to infer the volume from a single passive imaging device.

One illustrative occluding boundary algorithm is physics-based and employs a model of the elasticity, shape, and manufacturing tolerance of the inflatable element. This direct model is a predictive model that predicts the shape of the silhouette (occluding boundary) for any given volume. Since this predictive model depends on the distance between the element and the camera, the distance between the element, e.g. balloon, and the camera has to be kept within bounds specified a-priori. The inverse occluding boundary algorithm is a predictive model that predicts the volume of the disposable balloon based on the shape of the occluding boundary. A variational optimization algorithm is used, in which the occluding boundary is captured and the model parameter volume is determined by minimizing the discrepancy between the predicted silhouette, and the actual measured silhouette. As in most monocular computer-vision applications, there is an overall scale factor ambiguity due to the distance of the camera from the volume element. This ambiguity can be disambiguated by placing the patient in a pre-set location that corresponds to a known distance from the camera, or by placing the inflatable element in a calibrated context where other elements that are co-visible in the image have known scale. This may include the size of the skeleton of the inflatable element, or of the mouthpiece, or other element.

Another illustrative occluding boundary algorithm determines the three-dimensional volume from the two-dimensional silhouette and is based on learning algorithms. During a first training phase, calibrated quantities of gas are injected into the element(s), and their silhouettes measured accurately. This process is repeated for multiple elements, and multiple volumes, thus yielding a distribution of silhouettes for each volume. Such data is aggregated into a probability density or probability distribution function that represents the outcome of the training or calibration phase. During the testing phase, the system is presented with a new silhouette. The maximum a-posteriori value of the volume can then be computed using standard tools from Bayesian statistical estimation. This approach provides not only an estimate of the volume, but also the uncertainty in said estimate. This can guide the manufacturing process, for instance by requiring that the uncertainty be smaller than the tolerances imposed by the American Thoracic Society (ATS) and European Respiratory Society (ERS): "3% of reading or +/−50 ml, whichever is greater" (Standardisation of spirometry, M. R. Miller, J. Hankinson, V. Brusasco et al.; Eur Respir J 2005; 26: 319-338.

Another illustrative algorithm includes subjecting a uniform color balloon to image processing and includes the constant-color balloon and a color filter to facilitate the localization of the balloon in an image, via a Laplacian-of-Gaussian (LoG) or difference-of-Gaussian (DoG) filter as described by T. Linderberg, Principles for Automatic Scale Selection, Technical Report, KTH, Stockholm, CVAP, 1988. Alternative image segmentation algorithms, based on color, intensity or combination of other cues, can also be employed in alternative. Once the "color blob" has been located in an image, its boundary needs to be precisely localized. Blob detection can be performed at multiple scales to enable operating with inflatable elements of different scale and/or different size. For this, one can use region-based segmentation algorithms that are insensitive to the background, specifically the approach referred to as the "curious active contour," where a partial differential equation (PDE) is solved starting from an initial condition corresponding to the detected blob, and evolves outwards until the boundary is localized. See G. Sundaramoorthi, S. Soatto, and A. Yezzi, Curious Snakes: A Minimum-Latency Solution to the Cluttered Background Problem in Active Contours. Proc. Of the IEEE Intl. Conf. on Comp. Vis. And Patt. Recog., 2010. This approach enables accurate segmentation even when the background against which the balloon is placed is complex and cluttered, including regions of similar color of the original balloon.

It shall be appreciated by those of ordinary skill in the art that an empirical evaluation of the performance of the algorithm in terms of localization accuracy of the boundary, as a function of resolution of the camera, distance from the balloon, number of iterations in the curious active contour, and size of the grid where the equation is solved, needs to be performed to guarantee that the design of the system (the distance between the sensor and the patient, and the camera specifications) allows to meet and exceed the specifications of the ATS in terms of accuracy and precision.

During image processing, measurements of irradiance (light intensity) are converted into estimates of two-dimensional (2D) geometry (the trace on the image plane of the occluding contour of the volume element, or the position of salient point features on the inflatable element, or the profile of the grid), and then converted into the three-dimensional (3D) volume of the disposable volume spirometry apparatus. This step must include specific assumptions on the disposable device. For instance, region-based segmentation algorithms can be utilized if the device is designed and manufactured to have constant radiance (e.g. color), and calibrated, whereas feature detection and tracking algorithms can be used if the device is designed and manufactured to have non-constant radiance, but instead high-contrast regions (e.g. a grid or checkerboard pattern). See Jackson, Yezzi and Soatto, DYNAMIC SHAPE AND APPEARANCE MODELING VIA MOVING AND DEFORMING LAYERS, International Journal of Computer Vision, 2008, pp. 71-84, August, Vol. 79(1). Such high-contrast regions need to be photometrically salient, not necessarily geometrically regular.

The patterned balloon embodiment facilitates detection and estimation of the silhouette because the image of the patterned balloon includes a number of "distinctive features" that provide photometrically salient points. The patterned balloon can be manufactured by printing a grid, or blobs, on the balloon. Although the printed grid lines of blobs will deform, the deformation is constrained to remain on the surface of the balloon. Various "feature detection algorithms" can be employed to detect such salient features on the image and track them over time. A more detailed description of the feature detection algorithms is provided in the paper "Learning and matching multi-scale template descriptors for real-time detection, localization and tracking", T. Lee, S. Soatto, submitted to Image and Vision Computing, 2011, which is hereby incorporated by reference.

The feature detection algorithms can provide a collection of trajectories in two dimensions that can then be used either (a) to interpolate a prior model of the deformation of the balloon (e.g. through its mechanical properties, or (b) to infer the three-dimensional model via maximum-likelihood or maximum a-posteriori Bayesian inference based on previously collected training data, or (c) to establish correspondence in two or more cameras (stereo, or multi-view stereo) and estimate the 3D position of said points, from which the volume of the device can be computed using standard techniques as described above.

These algorithms may be used in a monocular (one sensor only) embodiment and a multi-ocular embodiment, e.g. binocular embodiment.

In the monocular embodiment, the disposable volume spirometry apparatus can be designed in such a way as to provide an accurate estimate of scale. Scale refers to the distance between the disposable volume spirometry apparatus and the camera. For example, the rigid mouthpiece can be color-coded in such a way that it is easily detected, and manufactured in a standard and known size, so that the size of its projection onto the image plane can be used to infer absolute scale of the distance between the mouthpiece and the camera. In the monocular embodiment, a calibrated model of the deformation of the disposable volume spirometry apparatus is generated. Additionally, an estimate of the volume change can be determined because of the monocular scaling effect of perspective projection, so that the absolute size depends on the distance from the volume element to the camera.

In addition to the unknown scale that can be addressed as shown above, the monocular embodiment includes a mathematical model of the deformation of the balloon that has to be employed in order to arrive at an estimate of 3D volume from measurements of the location of the silhouette on the image plane. An elastic model of the disposable volume spirometry apparatus can be derived from standard elastic partial differential equations, with a collection of parameters identified during a calibration procedure as part of the manufacturing process. These parameters affect both the 3D volume and the 2D silhouette. Therefore, once the dependency of the deformation on these parameter is known, the inverse problem of estimating the parameters from the silhouette can be solved, for instance via non-linear optimization, and the forward model can then be used to infer the volume, as a function of the estimated parameters.

In the binocular embodiment or multi-ocular embodiment, cameras can be pre-calibrated and triangulation methods can be used to provide a 3-D position at the correct scale. Additionally, the 2D trajectories of point features corresponding to the multi-ocular embodiments can be used to infer their 3D position, which in turn can be used to interpolate a model of the volume of the balloon.

As an alternate embodiment, a multi-camera rig (an arrangement of two or more cameras that are in known position and orientation relative to each other) can be employed to determine the position of such feature points in 3-D, without the need to accurately control the manufacturing process. Instead, simple interpolation procedures can be implemented to interpolate a surface between such feature points (e.g. via standard triangulation, as described by Ma et al., 2003), and therefore a numerical approximation of the volume can be computed.

The disposable volume spirometry apparatus may also be analyzed using a structured illumination embodiment whereby one or more cameras and an active illuminator and software algorithms provide the triangulation between the structured light and the imager. The structured illumination embodiment may be implemented using the KINECT® console sold by Microsoft Corp. In the structured illumination embodiment, the volume is extrapolated from the three-dimensional estimate of the visible portion of the inflatable element. Note that it cannot be simply assumed that the visible portion is half of the element because of perspective effects that are more pronounced the closer the camera is to the sensor. However, the tangents to the surface at the occluding boundaries allow determining the distance from the silhouette (occluding contour) to the symmetry plane of the inflatable element, and therefore extrapolate the volume reading to high accuracy. This calculation may be performed by analyzing the profile of the tangent vectors at the occluding boundaries that can be matched to the visible portion of the balloon along the plane orthogonal to the image plane, then the volume of the missing piece can be completed by symmetry.

Range imaging refers to a collection of techniques that are used to produce a 2D/3D image showing the distance points in a scene from a specific point, normally associated with some type of sensor device. The resulting image, the range image, has pixel values which correspond to the distance, e.g. brighter values mean shorter distance, or vice versa. If the sensor used to produce the range image is properly calibrated, the pixel values can be given directly in physical units such as meters.

The sensor device which is used for producing the range image is referred to as a range camera. Range cameras can operate according to a number of different techniques including, but not limited to, structured light, time-of-flight, stereo triangulation, sheet of light triangulation, interferometry, and coded aperture. Time-of-flight techniques can also be used to measure depth where a light pulse is used instead of an RF pulse, and results in a range image that is similar to a radar or LIDAR image.

Structured light operates by illuminating the scene with a specially designed light pattern. Depth can be determined using only a single image of the reflected light. The structured light can be in the form of horizontal and vertical lines, points, or checkerboard patterns. A structured-light 3D scanner is a device for measuring the three-dimensional shape of an object using the projected light patterns and a camera system. There are multiple variants of structured light projection.

The KINECT® camera from Microsoft Corp. includes an illustrative structured light range sensor that uses a continuously project infrared structured light. The KINECT® includes an RBG camera, 3D range sensor and multi-array microphone. The 3D range sensor includes an infrared laser projector and a monochrome CMOS sensor that captures video data in 3D under ambient light conditions. The sensing range of the depth sensor is adjustable and the KINECT® software is capable of automatically calibrating the sensor based on the physical environment.

As an alternative to structured-light sensors, other range sensors can be used such as optical time-of-flight sensors manufactured by CANESTA®, light detection and ranging (LIDAR) sensors that illuminate a target with light using laser pulses, of the combination thereof. Regardless of the sensor used, the algorithm or algorithms used must address discrepancies between the occlusion boundary and the symmetry plane.

In the case of time-of-flight, structured light, LIDAR, or other range sensor, an estimate of the geometry of the visible portion of the inflatable element is available directly. However, this needs to be processed in order to compute the volume of the occluded portion of the element. This can be done by considering the tangent vector to the surface at the occluding boundary, matching half of this with the visible portion of the surface orthogonal to the image plane, then extrapolating the volume by symmetry of the inflatable element.

The disposable volume spirometry apparatus may also be related to a volume measurement by using calibration procedures that correspond to the physical characteristics of the patterned balloon. The physical properties include shape and material of the disposable patterned balloon. The calibration procedures can also include data-based interpolation that calibrates the patterned balloon with controlled volume injections and interpolation based on the imaging data. This calibration procedure is performed off-line prior to the deployment of the instrument, and is dependent on the physical characteristics of the disposable element, that therefore needs to be manufactured to specification.

As described above, this patent incorporates by reference a collection of articles co-authored by one or more of the co-inventors, describing image and video analysis techniques that can be employed as building blocks to design the methods and algorithms to measure the volume of the volume element, in a remote non-contact fashion using one or more cameras or other imaging device, including projection devices for the case of structured illumination, interfaced with a computer where software implementation of the algorithms described in this patent application are available.

The apparatus described herein is (a) accurate and precise enough to meet or exceed standards mandated by the American Thoracic Society (ATS), (b) isolate all portions of the instrument that are in contact with the patient, (c) be economical, so that the disposable parts should not exceed, over the lifetime of the instrument, the cost of a comparable instrument currently existing on the market, and ideally also (d) be portable so that in-field epidemiological studies can be performed.

It is to be understood that the detailed description of illustrative embodiments are provided for illustrative purposes. The scope of the claims is not limited to these specific embodiments or examples. Therefore, various structural limitations, elements, details, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A spirometry system comprising:
an expandable disposable volume spirometry apparatus that measures volume of air that is exhaled over time and includes a symmetric inflatable element;

a remote non-contact sensor configured to capture a plurality of images of the symmetric inflatable element in different states of filling levels;

a memory that stores the captured images;

a processor operatively coupled to the memory, the processor configured to:

automatically determine a volume of exhaled air enclosed by a surface of the symmetric inflatable element in the different states of filling levels by analyzing the capture images; and report the volume of exhaled air over time.

2. The spirometry system of claim 1, wherein the expandable disposable volume spirometry apparatus further comprises a first valve that allows air to enter the symmetric inflatable element.

3. The spirometry system of claim 2, wherein the expandable disposable volume spirometry apparatus further comprises, a filter element that captures at least one exhaled compound selected from the group consisting of carbon dioxide, carbon monoxide, nitrogen oxide, exhaled breath condensate (EBC), volatile organic compounds (VOC), breath trace element, and breath biological fragments; and a second valve that allows air to exit the symmetric inflatable element.

4. The spirometry system of claim 3 wherein the carbon dioxide associated with an exhaled gas mixture passes the first valve and enters the symmetric inflatable element and is captured by the filter element before the second valve allows the exhaled gas mixture to exit the symmetric inflatable element.

5. The spirometry system of claim 1 further comprising a projector that generates a light pattern that is projected on the symmetric inflatable element, and the remote non-contact sensor captures the images of the light pattern projected on the symmetric inflatable element, analyzing the surface of the of the symmetric inflatable element gathered from the remote non-contact sensor.

6. The spirometry system of claim 5 wherein the volume of the symmetric inflatable element is extrapolated from a three-dimensional estimate of the symmetric inflatable element.

7. The spirometry system of claim 1 further comprising, a background that is detached from the disposable spirometry apparatus and provides a surface for receiving an occluding boundary of the inflatable element projected on the background, and the remote non-contact sensor includes a digital camera that captures the occluding boundary projected on the background.

8. The spirometry system of claim 1 wherein the remote non-contact sensor includes a range sensor for capturing the plurality of images.

9. The spirometry system of claim 1 wherein the remote non-contact sensor includes a laser for capturing the plurality of images.

10. The spirometry system of claim 1 wherein the remote non-contact sensor includes a radar for capturing the plurality of images.

11. The spirometry system of claim 1 further comprising a plurality of remote non-contact sensors for capturing the plurality of images communicatively coupled to the processor and the memory.

12. A spirometry system comprising:

an expandable disposable volume spirometry apparatus that measures the volume of air that is exhaled over time and includes, a symmetric inflatable element, a first valve that allows exhaled air to enter the symmetric inflatable element, a filter element that captures at least one exhaled compound selected from the group consisting of carbon dioxide, carbon monoxide, nitrogen oxide, exhaled breath condensate (EBC), volatile organic compounds (VOC), breath trace element, and breath biological fragments, and a second valve that allows air to exit the symmetric inflatable element;

a remote non-contact sensor configured to capture a plurality of images of the symmetric inflatable element in different states of filling levels;

a memory that stores the captured images;

a processor operatively coupled to the memory, the processor configured to automatically determine a volume of exhaled air enclosed by a surface of the symmetric inflatable element in the different states of filling levels by analyzing the captured images; and report the volume of exhaled air over time.

13. The spirometry system of claim 12 wherein the carbon dioxide associated with an exhaled gas mixture passes the first valve and enters the symmetric inflatable element and is captured by the filter element before the second valve allows the exhaled gas mixture to exit the symmetric inflatable element.

14. The spirometry system of claim 12 further comprising a projector that generates a light pattern that is projected on the symmetric inflatable element, the remote non-contact sensor captures the images of the light pattern projected on the symmetric inflatable element, and the processor determines the volume of the symmetric inflatable element.

15. The spirometry system of claim 14 wherein the volume of the symmetric inflatable element is extrapolated from a three-dimensional estimate of the symmetric inflatable element.

16. The spirometry system of claim 12 further comprising, a background that is detached from the disposable spirometry apparatus and provides a surface for receiving an occluding boundary of the inflatable element projected on the background, and the remote non-contact sensor includes a digital camera that captures ag the occluding boundary projected on the background.

17. A spirometry system comprising:

an expandable disposable volume spirometry apparatus that measures volume of air that is exhaled over time and includes a symmetric inflatable element;

a projector that generates a light pattern that is projected on the symmetric inflatable element;

a remote non-contact sensor that captures the images of the light pattern projected on the symmetric inflatable element;

a memory that stores the captured images;

a processor operatively coupled to the memory, the processor configured to
automatically determine a volume of exhaled air enclosed by a surface of the symmetric inflatable element in the different states of filling levels by analyzing the captured images; and
report the volume of exhaled air over time.

18. The spirometry system of claim 17, wherein the expandable disposable volume spirometry apparatus further comprises a first valve that allows air to enter the symmetric inflatable element.

19. The spirometry system of claim 18, wherein the expandable disposable volume spirometry apparatus further comprises,
a filter element that captures carbon dioxide; and
a second valve that allows air to exit the symmetric inflatable element.

20. The spirometry system of claim 19 wherein the carbon dioxide associated with an exhaled gas mixture passes the first valve and enters the symmetric inflatable element and is captured by the filter element before the second valve allows the exhaled gas mixture to exit the symmetric inflatable element.

* * * * *